United States Patent [19]
Drake

[11] Patent Number: 4,793,474
[45] Date of Patent: Dec. 27, 1988

[54] CONTROLLED DELIVERY AGRICULTURAL CAPSULE AND METHOD OF MAKING

[75] Inventor: Cyril F. Drake, Harlow, England

[73] Assignee: International Standard Electric Corporation, New York, N.Y.

[21] Appl. No.: 354,442

[22] Filed: Mar. 3, 1982

[30] Foreign Application Priority Data

Mar. 5, 1981 [GB] United Kingdom ............... 8107005

[51] Int. Cl.⁴ .................. A01M 25/00; B65B 9/10
[52] U.S. Cl. ........................... 206/0.5; 43/124; 43/131; 53/474; 53/561; 53/567; 71/64.11; 220/DIG. 30
[58] Field of Search ............ 206/0.5; 220/DIG. 30; 43/124, 131, 126; 53/140, 561, 567, 474, 445; 71/64.11, 69.1, 32; 424/1

[56] References Cited

U.S. PATENT DOCUMENTS

| | | | |
|---|---|---|---|
| 1,831,476 | 11/1931 | Bennett | 220/DIG. 30 |
| 2,750,027 | 6/1956 | Cummings | 206/0.5 |
| 2,915,386 | 12/1959 | Strauss | 206/526 |
| 3,400,011 | 9/1968 | Fox | 71/64.11 |
| 3,754,871 | 8/1973 | Hessel et al. | 206/0.5 |
| 3,832,827 | 9/1974 | Lemelson | 53/140 X |
| 3,930,833 | 1/1976 | Roberts | 71/64.1 |
| 3,958,973 | 5/1976 | Roberts | 71/64.1 |
| 4,123,248 | 10/1978 | Drake | 71/32 |
| 4,148,623 | 4/1979 | Drake | 71/32 |
| 4,198,782 | 4/1980 | Kydonieus et al. | 43/124 |
| 4,350,675 | 9/1982 | Drake | 424/1 |

*Primary Examiner*—Stephen Marcus
*Assistant Examiner*—Bryon Gehman
*Attorney, Agent, or Firm*—T. L. Peterson

[57] ABSTRACT

A capsule for the controlled release of an active material, e.g. into soil, is described. The capsule comprises an insoluble tubular housing (11) containing a number of water soluble or biodegradable partition walls (13) defining one or more hermetically sealed compartments, (12) filled with the active material (14), e.g. an insecticide. When the capsule is in contact with water or an aqueous medium the partition walls (13) slowly dissolve or degrade thus releasing the active material after a predetermined delay.

5 Claims, 1 Drawing Sheet

CONTROLLED DELIVERY AGRICULTURAL CAPSULE AND METHOD OF MAKING

This invention relates to devices for releasing controlled quantities of an active material, and in particular to capsules for releasing active materials, e.g. pesticides, into soil or an aqueous medium.

Active materials such as pesticides are generally applied to growing crops and/or to the soil in the form of sprays or dusting powders. Crop spraying and dusting are relatively costly operations. The conventional techniques involve a high investment in application equipment and a large proportion of the applied material is in fact ineffective as it is lost either by drifting away from the application site or by failure to deposit on the particular treatment point required. Thus, when applying such a material to a growing crop and/or to the soil, a considerable degree of 'overkill' must be allowed for. Not only is this needlessly expensive in the use of materials but it is also environmentally undesirable. Spray or dust drift can damage plants and/or animals adjacent the treated region. There is also considerable concern that the excessive quantities of active materials required with present techniques can build up the soil and cause permanent environmental damage.

A further disadvantage of the conventional methods of application is that the material supplied in such ways are of course active immediately and so have to be applied obligatorily at the time when, or not long before, they are needed. It is thus not, for example, possible to apply a material when a crop is planted and for the material to remain inert until the time of rapid growth of the crop when it may be needed most.

Furthermore, means have been described, hitherto, of preparing controlled or delayed release materials, but products of such a type suffer from one or more of the following disadvantages: they are too expensive to be cost-effective; the rate of release or delay-time is not reproducible; or the delivery-system cannot be used when it is necessary to disperse material uniformly over a large area.

The object of the present invention is to minimise or to overcome these disadvantages.

According to one aspect of the invention there is provided a device for the controlled release of one or more active materials, including a water insoluble body having one or more compartments each for receiving a quantity of the active material and each sealed by a partition formed from a water soluble or biodegradable material.

According to another aspect of the invention there is provided a method of making a device for the controlled release of active materials, said method including extruding a plastic tube, and simultaneously filling the tube bore with water soluble or biodegradable cylindrical bodies of substantially the same diameter as the tube and interposed with quantities of the active material so as to provide a tube having a plurality of hermetically sealed compartments each of which containing active material, and cutting said filled tube into portions each of which contains at least one said compartment.

According to a further aspect of the invention there is provided an apparatus for manufacturing devices for the controlled release of active material, including means for extruding a tube of a plastic material, means for filling said tube with a plurality of cylindrical bodies of a water soluble or biodegradable material of substantially the same diameter as the tube and interposed with quantities of active material so as to define a plurality of hermetically sealed compartments each of which contains the active material, and means for sectioning the filled tube into portions each of which contains at least one of said components.

The techniques described herein provide a controlled delivery system wherein the active material is released selectively and at a predetermined period after application. For example, pesticides for agricultural crops can be dispensed by sowing the encapsulated pesticide at the same time as the seed. Release of the pesticide is timed to take place at a particular stage of the crop development, e.g. when attack by a pest is expected. In particular the release of the active material can be present to coincide with the breeding cycle of the pest to be controlled.

In a further embodiment a plurality of pesticidal materials may be encapsulated in a single capsule, each material occupying a separate compartment of the capsule. Release of the contents of each individual compartment can be timed to coincide with various stages of growth of a crop.

The term 'pest' as employed herein refers not only to the more common insect predators but is also understood to include other animal predators such as nematodes and molluscs, and disease predators such as fungi and bacteria.

In another embodiment a pest-attractant is included in one capsule and a biocidal material is included in another compartment of the same or of a separate capsule the composite system being so designed that the release of the attractant is effectively co-temporal with the release of the biocide. An example is the control of bilharzia by the inclusion of one of the known water-snail attractants such as the aliphatic acids and a suitable molluscide as the biocide, the system being used in water bodies infested with water snails which act as vectors for the schistosome parasite.

In yet another embodiment the body of the capsule is made of a biologically inert plastic, and the capsule is implanted in an animal or human. The active material can be released in a single pulse at a predetermined time after implantation or in a series of pulses at predetermined intervals. The active material can be, for example, a pharmaceutical, a hormone, an antibiotic, or a parasiticide.

Embodiments of the invention will now be described with reference to the accompanying drawings in which.

Figure 1:
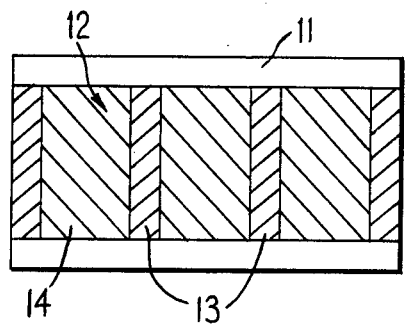
FIG. 1 is a sectioned view of a capsule for releasing an active material.
Figure 2:
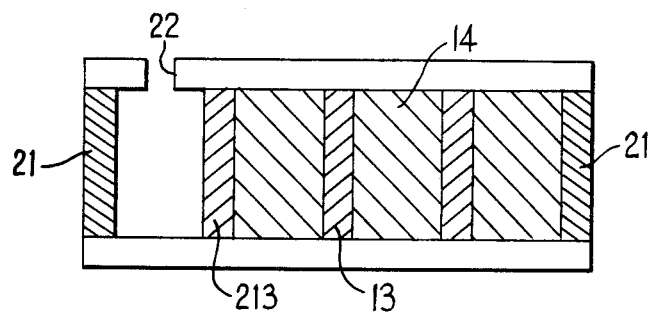
FIGS. 2 and 3 are sectioned views of two further forms of the capsule of FIG. 1.
Figure 3:
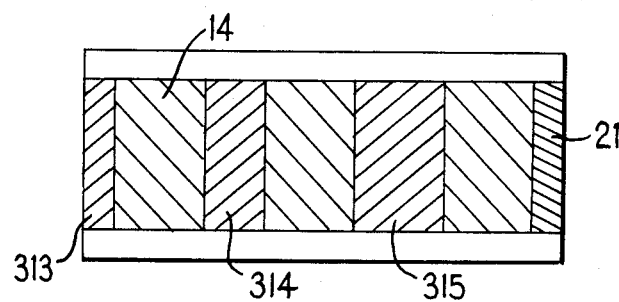
Figure 4:
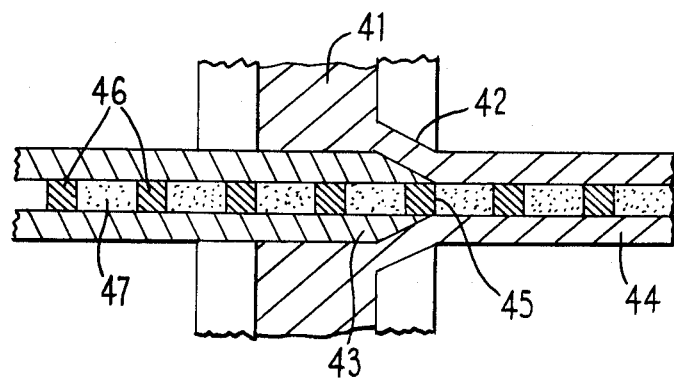

and FIG. 4 is a schematic diagram of an apparatus for manufacturing the capsules of FIGS. 1, 2 and 3.

Referring to FIG. 1, the capsule comprises a tubular housing 11 of a water insoluble material, preferably made of a plastic material such as polyvinyl chloride (PVC), having one or more hermetically sealed compartments 12 therein defined by partition walls 13. Each compartment 12 contains a quantity of an active material 14, e.g. a pesticide. The partition walls 13 are made of a water soluble material or of a biodegradable material. Advantageously the partition walls 13 are made of a water soluble glass composition. This typically comprises a glass forming oxide together with one or more glass modifying oxides.

The capsules are dispersed on to or into soil either by being broadcast or, advantageously, by 'sowing' together with the seed of an agricultural crop to be protected. The partition walls 13 are then slowly dissolved by soil moisture, the rate at which dissolution is effected being determined by the water solubility of the wall material. The time taken for complete dissolution to release the capsule contents is determined by the thickness and composition of the partition wall 13.

By suitable choice of partition wall thickness and dissolution rate the period between application of the capsules and release of their contents can be adjusted to coincide with a predetermined treatment timetable.

As previously stated we prefer to construct the partitions 13 from a soluble glass comprising a glass forming oxide together with one or more glass modifying oxides. A glass forming oxide is defined as an oxide, for example phosphorus pentoxide or boric oxide, which is capable of forming a glass without the addition of further materials. A glass modifying oxide is defined as an oxide which, whilst it is not capable of itself of forming a glass, can form a glass in association with a glass forming oxide. The addition of a glass modifying oxide to a glass forming oxide modifies the physical properties of the latter. In particular the formation of a glass from a glass forming oxide and a glass modifying oxide produces a material having water dissolution properties differing from those of the glass former alone.

Some glass modifying oxides have a comparatively small effect on the dissolution rate of the glass former whilst others have a relatively large effect. It is thus possible to produce glasses over a wide range of composition and dissolution rates. Furthermore, when a composition having a dissolution rate near to a desired value has been formed, final adjustment may be made by adding small quantities of particular dissolution rate determining oxides. For example we have found that the dissolution rate of a glass can be decreased by the incorporation of alumina or an oxide of a Group II metal. The technique of glass dissolution rate control is more fully described in our co-pending U.S. application Ser. No. 180,068, now U.S. Pat. 4,350,675.

For the purposes described herein we prefer to employ glasses incorporating phosphorus pentoxide as the glass forming oxide. Suitable glass modifying oxides include, but are in no way limited to, calcium oxide, magnesium oxide, zinc oxide, alkali metal oxide, and alumina.

It will be clear to those skilled in the art that although oxide glasses are referred to their precursory materials need not be in the oxide form. It will also be clear that though the constituents of an oxide glass are described as and quantitively analysed as oxides, the discreet stoichiometric oxides are not necessarily present.

An alternative capsule is shown in FIG. 2. In this arrangement the tube ends are sealed each with an insoluble plug 21, the space within the tube being divided by soluble partition walls 13, 213 into compartments 12 as before. One end of compartment 12 is provided with an opening 22 whereby soil moisture can enter the capsule to attack the exposed partition wall 213. After this wall 213 has dissolved releasing the contents of the first compartment the next wall 13 is exposed to attack and so on. In this way release of the active material 14 occurs as a series of bursts.

The capsule shown in FIG. 3 is designed to release its compartment contents with an increased delay between successive releases. The compartment walls 313, 314, 315 are of increasing thickness so that dissolution to expose each compartment takes successively longer periods of time. To ensure that dissolution takes place from one end only of the tube the other end is sealed with an insoluble plug 21.

The active material contained in the compartment 12 of the capsules of FIGS. 1, 2 and 3 may comprise, but is not limited to, an insecticide, a fungicide, a fertiliser or mixtures thereof. In a further embodiment the partition walls 13 themselves may also contain an active material. For example the walls may incorporate copper which acts as a fungicide and a molluscide, or they may incorporate one or more trace elements necessary for successful crop production. In another application, where the capsules are to be employed in an arid enviornment, one or more compartments may contain water so that dissolution of the walls 13 to release the active material is effected internally.

FIG. 4 is a schematic diagram of an apparatus for manufacturing the capsules of FIGS. 1, 2 or 3. The apparatus is based on a plastic melt extruder and includes a chamber 41 from which molten plastic material, for example PVC, is extruded under pressure via a die 42 and nozzle 43 to form a tube 44.

The extruder nozzle 43 has an opening 45 through which soluble (e.g. glass) cylindrical members 46 interposed with measured quantities of an active material 47 are fed at a rate corresponding to the rate at which the tube 45 is extruded. The extruded tube is cooled and is then sectioned into suitable lengths to produce the finished capsules.

In some applications the nozzle 43 may be cooled to prevent thermal decomposition of the active material. However, as the passage of the material through the point will be rapid, in many applications cooling of the nozzle will not be necessary.

Other methods of manufacture will be clear to those skilled in the art and the technique is not limited to the method of manufacture nor to the details of the geometry of the capsule both of which are described here merely by way of illustration.

In a further process lengths of plastic tubing may be sealed at one end and then filled with the active material in a similar manner in which medicinal capsules are filled. A soluble glass plug is then inserted to provide a seal with the plastic tube so as to retain the material.

It should be noted that the term 'insoluble' used herein with reference to the tubular housing is not intended to mean that the housing must be completely insoluble. The term is also understood to include cases where the housing is in fact soluble or biodegradable but at a rate sufficiently low that the housing remains in being until the active material has been released by disolution or degradation of the partition walls.

I claim:

1. An agricultural capsule for the controlled release of an active material selected from the group consisting of an insecticide, a nematocide, a molluscide, a fungicide, a fertilizer, a pest attractant and mixtures thereof, said capsule comprising a water insoluble plastic tube, a plurality of spaced water soluble glass cylindrical partition bodies positioned in said tube, said glass containing phosphorus pentoxide or boric oxide as its principal glass forming oxide, said glass partition bodies dividing the tube bore into a plurality of hermetically sealed compartments, each compartment containing said active material, at least one wall of each compartment being said glass partition, the outer wall of each compartment being said insoluble tubing, and wherein the dissolution rate of the glass bodies is such that, when the capsule is contacted with water or moisture, the glass bodies dissolve over a period to time to release the active material contained in the compartments.

2. A capsule as claimed in claim 1 wherein said plastic material is polyvinyl chloride.

3. The capsule of claim 1 in which the ends of said tube are sealed with a water insoluble plug and the outer wall of one of the said compartments has an opening therein for the entrance of water or moisture.

4. The capsule of claim 1 in which one end of said tube is sealed with a water insoluble plug and said glass cylindrical partitions are of varying thickness beginning with the end opposite the plug.

5. A method of making a capsule for the controlled release of an active material selected from the group consisting of an insecticide, a nematocide, a molluscide, a fungicide, a fertilizer, a pest attractant and mixtures thereof said method including extruding a water insoluble plastic tube, and simultaneously filling the tube bore with water soluble glass cylindrical partition bodies interposed with measured quantities of active material, said glass containing phosphorus pentoxide or boric oxide as its principal glass forming oxide, said glass partition bodies being of substantially the same diameter as the bore to provide a tube having a plurality of hermetically sealed compartments each of which contains the active material, and cutting said filled tube into portions each of which contains a plurality of said compartments.

* * * * *